(12) United States Patent
Malinsky

(10) Patent No.: US 11,266,541 B2
(45) Date of Patent: Mar. 8, 2022

(54) LOWER EXTREMITY GARMENT AND METHOD OF USE FOR ELDERLY AND THE LIKE

(71) Applicant: Svetlana Malinsky, Germantown, MD (US)

(72) Inventor: Svetlana Malinsky, Germantown, MD (US)

(*) Notice: Subject to any disclaimer, the term of this patent is extended or adjusted under 35 U.S.C. 154(b) by 398 days.

(21) Appl. No.: 16/004,862

(22) Filed: Jun. 11, 2018

(65) Prior Publication Data
US 2019/0008693 A1 Jan. 10, 2019

Related U.S. Application Data

(60) Provisional application No. 62/517,913, filed on Jun. 10, 2017.

(51) Int. Cl.
*A61F 5/05* (2006.01)
*A61F 13/08* (2006.01)
(Continued)

(52) U.S. Cl.
CPC ............ *A61F 13/08* (2013.01); *A61F 5/0127* (2013.01); *A61H 1/008* (2013.01);
(Continued)

(58) Field of Classification Search
CPC ...... A61F 13/08; A61F 5/0127; A61F 5/0195; A61F 5/0585; A61F 5/0111;
(Continued)

(56) References Cited

U.S. PATENT DOCUMENTS 4,791,736 A   12/1988 Phillips
4,938,777 A * 7/1990 Mason .................. A61F 5/0113
                                                         602/27
(Continued)

OTHER PUBLICATIONS

Bauerfeind Sports Ankle Support, Amazon.com (date(s) = unknown, printed Apr. 3, 2017).
(Continued)

*Primary Examiner* — Camtu T Nguyen
(74) *Attorney, Agent, or Firm* — Westerman, Hattori, Daniels & Adrian, LLP

(57) ABSTRACT

According to some embodiments, a lower extremity garment is provided that includes: a flexible sock portion configured to surround at least a user's foot and ankle including the user's toes, the flexible sock portion having a substantially L-shape with a base portion for receiving a user's foot and a leg portion extending transverse from the base portion for receiving a user's lower leg; a semi-rigid support member integrated with the sock in the leg portion and configured to surround only a rear portion of the user's leg when worn including from the user's heel up to a position above the user's ankle, while remaining open and not extending around a forward side of the leg portion; a semi-rigid foot pad portion integrated with the sock in the foot portion and configured to support a bottom of a user's foot when worn; and at least one strap member configured to surround the leg portion when worn, wherein the at least one strap member includes at least one adjustable strap member.

25 Claims, 15 Drawing Sheets

(51) Int. Cl.
*A61F 5/01* (2006.01)
*A61H 1/00* (2006.01)

(52) U.S. Cl.
CPC .. *A61H 2201/164* (2013.01); *A61H 2201/165* (2013.01); *A61H 2205/106* (2013.01); *A61H 2209/00* (2013.01)

(58) Field of Classification Search
CPC ............ A61F 5/0113; A61H 2201/164; A61H 2201/165; A61H 2205/106; A61H 2209/00; A41B 11/10; A41B 11/007
See application file for complete search history.

(56) References Cited

U.S. PATENT DOCUMENTS

| | | | |
|---|---|---|---|
| 5,430,960 | A | 7/1995 | Richardson |
| 5,617,745 | A | 4/1997 | Della Corte et al. |
| 5,713,143 | A | 2/1998 | Kendall |
| 6,038,793 | A | 3/2000 | Kendall |
| 6,101,655 | A | 8/2000 | Buddle |
| 6,125,557 | A | 10/2000 | Brown |
| 6,269,555 | B1 | 8/2001 | Brown |
| 6,315,786 | B1 | 11/2001 | Smuckler |
| 6,361,514 | B1 * | 3/2002 | Brown .................. A61F 5/0111 128/882 |
| 6,601,320 | B1 | 8/2003 | Brown |
| 6,641,550 | B1 | 11/2003 | Johnson |
| 7,694,437 | B2 | 4/2010 | Hogan |
| 8,505,120 | B2 | 8/2013 | Lambertz |
| 8,918,917 | B2 | 12/2014 | Nordstrom et al. |
| 9,072,339 | B2 | 7/2015 | Manolian et al. |
| 9,131,746 | B2 | 9/2015 | Arciuolo |
| 2006/0026740 | A1 * | 2/2006 | Vargas .................. A43B 7/146 2/239 |
| 2013/0060181 | A1 * | 3/2013 | Fontaine ............... A61F 13/064 602/30 |
| 2014/0230131 | A1 | 8/2014 | Alston |
| 2014/0358057 | A1 * | 12/2014 | Bradshaw ............. A61F 5/0111 602/28 |
| 2016/0081836 | A1 | 3/2016 | Sawle et al. |
| 2016/0081840 | A1 | 3/2016 | Higgins |
| 2016/0278474 | A1 | 9/2016 | Davis et al. |
| 2016/0309794 | A1 * | 10/2016 | Nasser ................. A41B 11/005 |
| 2017/0127759 | A1 * | 5/2017 | Diemer ................. A43B 17/18 |
| 2018/0153716 | A1 * | 6/2018 | Martin ...................... A61F 2/78 |

OTHER PUBLICATIONS

Plantar Fasciitis Sock Sleeve with Ankle Brace Strap for Support & Pain Relief by Athledict, Amazon.com (date(s) = unknown, printed Apr. 3, 2017).

Liveup SPORTS Fitness Ankle Support Elastic Bandage Pressure Compression Sock for Running/Basketball, Amazon.com (Dates = unknown, printed Apr. 3, 2017).

Adjustable Position Foot Orthosis, RehabMart.com (date(s) = unknown, printed Apr. 3, 2017).

Dorsi-Flexion Multi Podus System, www.rehabmart.com <http://www.rehabmart.com> (date(s) = unknown, printed Apr. 3, 2017).

Donjoy Strapping Elastic Ankle Support, www.healthandcare.co.uk <http://www.healthandcare.co.uk>, (date(s) = unknown, printed Apr. 3, 2017).

C. S. Lim, MBBS PhD and A. H. Davies, DM, Graduated Compression Stockings, CMAJ, <https://www.ncbi.nlm.nih.gov/pmc/articles/PMC4081237/>, Jul. 8, 2014.

Ossur AFO dynamic foot drop brace, <http://e-medicalbroker.com/product-eng-4862-Ossur-AFO-R-dynamic-foot-drop-brace.html> (Date(s) = unknown).

Source Ortho Web Site, ProCare Super-Lite AFO Leaf Spring, <https://www.sourceortho.net/super-lite-afo-brace/> (Date(s) = unknown).

AFO Swedish LSO drop foot leg brace, Ebay, <http://www.ebay.com/itm/ANKLE-FOOT-ORTHOSIS-AFO-SWEDISH-LSO-DROP-FOOT-LEG-BRACE-/332200831927?var=&hash=item4d58b66bb7> (Date(s) = unknown).

RDX Reference 1 (date unknown), cite https://rdxsports.com/rdx-neoprene-anklet-socks-brace-support/#product_tabs_description_tabbed <https://rdxsports.com/rdx-neoprene-anklet-socks-brace-support/>.

RDX Reference 2 (date unknown), cite <https://rdxsports.com/rdx-neoprene-anklet-foot-support-brace-guard/>.

* cited by examiner

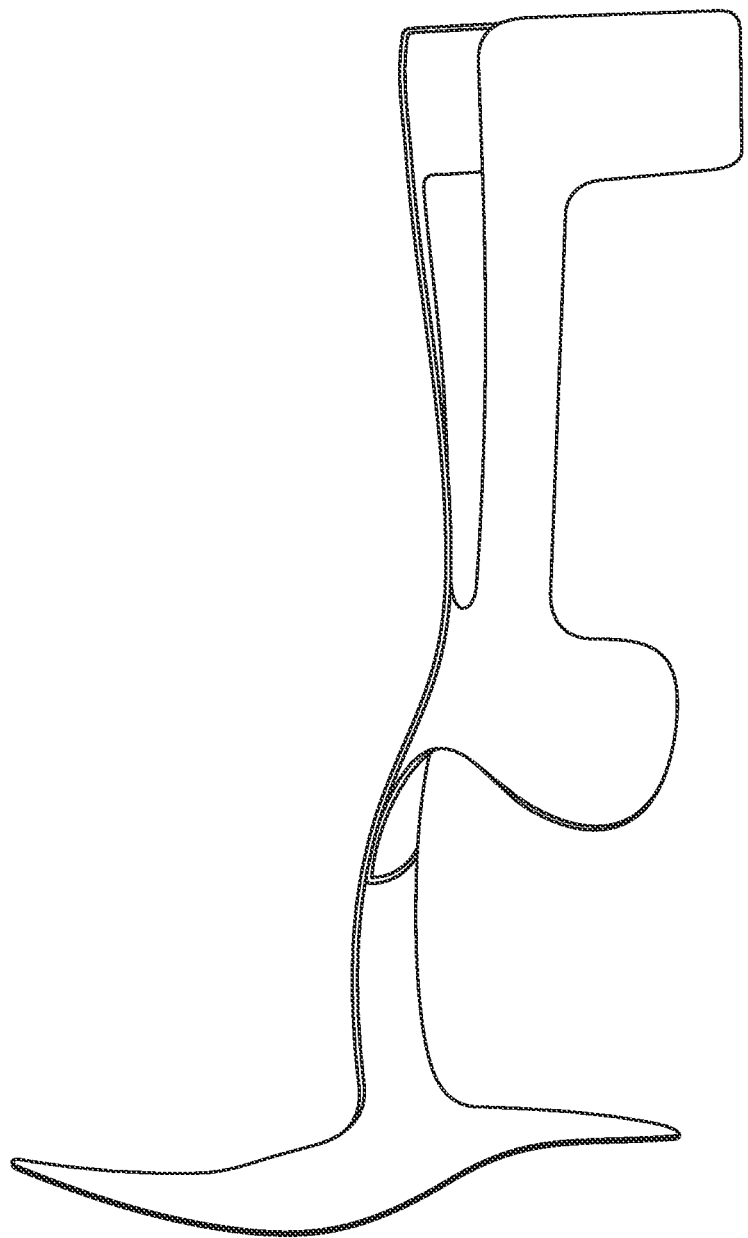
FIG. 8C(1)

FIG. 8C(2)

LOWER EXTREMITY GARMENT AND METHOD OF USE FOR ELDERLY AND THE LIKE

The present application is a non-provisional of U.S. application Ser. No. 62/517,913 entitled Lower Extremity Garment and Method of Use for Elderly and the Like, the entire disclosure of which is incorporated herein by reference as though recited herein in full.

BACKGROUND

Field of the Invention

The present application relates generally to garments and in particular to garments worn on the lower extremities, such as, e.g., the foot and ankle. In particular, the preferred embodiments provide novel ankle garments that address issues faced by elderly and the like.

Introduction

In modern society, it has become common place to wear garments covering the foot and ankle—e.g., socks. In general, socks provide a variety of purposes, including maintaining body warmth (e.g., inhibiting loss of heat from the foot to the air {e.g., convection} and loss of heat from the foot to the ground {e.g., conduction}) as well as protection from external objects.

In addition, socks have also been developed that provide a level of compression for medical purposes. See, e.g., C. S. Lim, MBBS PhD and A. H. Davies, D M, Graduated Compression Stockings, CMAJ, Jul. 8, 2014 (https://www.ncbi.nlm.nih.gov/pmc/articles/PMC4081237/). As indicated in this CMAJ article:

"Compression therapy is a frequently used physical therapy in conditions involving venous and lymphatic insufficiency in the lower limbs, including varicosities, lymphedema, venous eczema and ulceration, deep vein thrombosis and postthrombotic syndrome. The many forms of compression therapy include elastic and non-elastic bandages, boots, hosiery or stockings . . . , and pneumatic devices. Graduated compression stockings . . . are often prescribed and have the advantage of being more acceptable, relatively easier to put on and less cumbersome than bandaging and pneumatic devices."

As further indicated in this CMAJ article, some types of compression stockings include:

"Graduated or Medical Compression Stockings

Graduated compression stockings exert the greatest degree of compression at the ankle, and the level of compression gradually decreases up the garment They are often used to treat chronic venous disease and edema They are designed for ambulatory patients and are manufactured under strict medical and technical specifications, including consistency and durability, to provide a specific level of ankle pressure and graduation of compression Antiebmolism Stockings Antiembolism stockings are used to reduce the risk of deep vein thrombosis Like graduation compression stockings, they provide gradient compression They are designed for bedridden patients and do not meet the technical specifications for use by ambulatory patients Although the terms "antiembolism stockings" and "graduated compression hosiery" are often used interchangeably and both types of stockings offer graduated compression, they have different levels of compression and indications Nonmedical Support Hosiery Nonmedical support hosiery, including flight socks and elastic support stockings, are often used to provide relief for tired, heavy and aching legs They usually exert considerably less compression than graduated compression stockings The compression is uniform and not graduated They do not need to meet the strict medical and technical specifications as those of graduated compression stockings They can often be bought over the counter without a prescription"

Conventionally, when an individual injures an ankle or has compromised ankles and desires to take precautionary preventative measures, an individual may use an ankle brace and/or a wrap (such as, e.g., an ACE™ bandage) to provide additional support for the user's ankle.

However, conventional ankle braces have had a variety of limitations and do not address needs of the elderly and others with similar needs to the elderly.

For example, the present inventor has determined that conventional ankle braces often:

a) are difficult to put on;
b) are difficult to maintain (e.g., clean or wash);
c) are difficult to use along with other garments (e.g., socks and/or shoes);
d) are difficult to use while maintaining appropriate warmth and management of body temperature and air flow (e.g., not surrounding an entire foot, not covering toes and/or other portions, excessively obstructing air flow to some areas, creating excessive bulk that inhibits management of air flow using other garments such as, e.g., socks and/or shoes, etc.).

Accordingly, the present inventor has developed the present invention which overcomes various limitations of the existing art that has been discovered by the present inventor.

SUMMARY OF THE PREFERRED EMBODIMENTS

The preferred embodiments overcome the above and/or other problems in the background art.

According to some embodiments of the invention, a lower extremity garment is provided that includes: a flexible sock portion configured to surround at least a user's foot and ankle including the user's toes, the flexible sock portion having a substantially L-shape with a base portion for receiving a user's foot and a leg portion extending transverse from the base portion for receiving a user's lower leg; a semi-rigid support member integrated with the sock in the leg portion and configured to surround only a rear portion of the user's leg when worn including from the user's heel up to a position above the user's ankle, while remaining open and not extending around a forward side of the leg portion; a semi-rigid foot pad portion integrated with the sock in the foot portion and configured to support a bottom of a user's foot when worn; and at least one strap member configured to surround the leg portion when worn, wherein the at least one strap member includes at least one adjustable strap member.

In some embodiments, the flexible sock portion is configured to surround the user's entire foot and to extend above a height of the user's ankle.

In some embodiments, the garment is sized to be worn within footwear including shoes or sneakers.

In some embodiments, the garment is configured to have a width of less than 3.5 mm along lateral sides thereof.

In some embodiments, the garment is configured to have a width of less than 3 mm along lateral sides thereof.

In some embodiments, a method for supporting the ankle of a user is provided that includes placing the lower extremity garment on the lower leg of a user such as to reduce inversion and eversion of the user's heel and reduce the risk of falling.

In some embodiments, the method further includes providing dorsal assist of the user's ankle in the frontal plane with the lower extremity garment.

In some embodiments, the method further includes providing arch support for the user with the lower extremity garment.

In some embodiments, the method further includes providing cushioning under the sole of the user's foot with the lower extremity garment.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention are shown by a way of example, and not limitation, in the accompanying figures, in which:

FIGS. 8A to 8D show some illustrative existing supports structures that can be modified for implementation in some illustrative embodiments;

DETAILED DESCRIPTION OF THE PREFERRED EMBODIMENTS

While the present invention may be embodied in many different forms, the illustrative embodiments are described herein with the understanding that the present disclosure is to be considered as providing examples of the principles of the invention and that such examples are not intended to limit the invention to preferred embodiments described herein and/or illustrated herein.

The Preferred Embodiments

According to some illustrative embodiments of the invention, a garment for a lower extremity (e.g., a user's foot and ankle) is provided for use by elderly and/or others with similar issues to the elderly.

For example, many individuals within the elderly population are at an increased risk of falling due to weakened lower extremity musculature and decreased proprioception and/or ability to discern foot position in space.

In the preferred embodiments, a novel garment is provided in the form of a sock that has an incorporated support for the ankle. In the preferred embodiments, the incorporated support for the ankle is configured to reduce inversion and eversion of the heel. In this manner, the novel sock, thus, reduces the risk of falling due to, e.g., inversion sprains.

Figure 6:
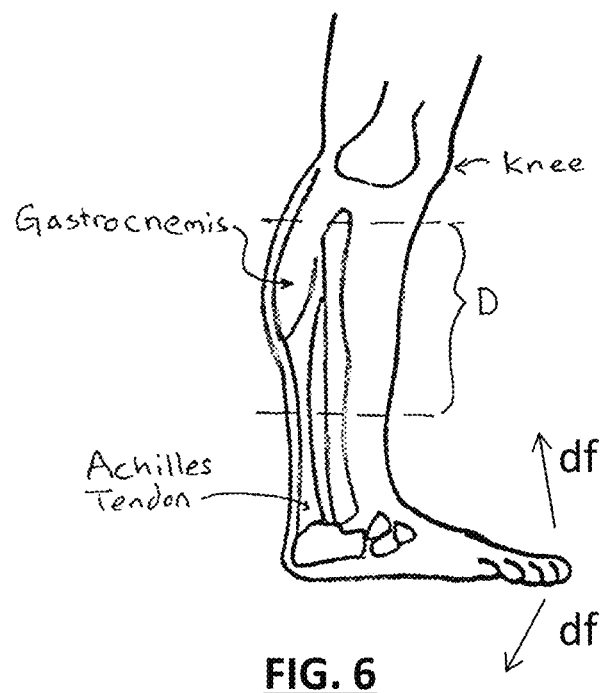
FIGS. 6 and 7 are explanatory figures depicting relationships of the garment in relation to a user's anatomy (e.g., leg in FIG. 6 and foot in FIG. 7) during use according to some illustrative embodiments of the invention.

In some preferred embodiments, the support of the garment is also configured to provide horizontal position stabilization or "dorsal assist" of the ankle in the frontal plane (e.g., assist lifting of the toes from falling downward in the direction of the downward arrow df shown in FIG. 6, such as, e.g., when an elderly person has diminished ability to maintain foot position due to weakening or paralysis or other condition).

In some preferred embodiments, the garment is also adapted to include an integrated arch support. In the preferred embodiments, the integrated arch support reduces the pull of the posterior tibial tendon, such as to reduce the risk of dysfunction of the tibial tendon.

In some preferred embodiments, the garment also includes additional cushioning under the sole of the user's foot in order to provide shock absorption and to off-load high pressure areas under the foot to reduce the risk of developing calluses that may lead to ulcerations or cause pain that can, e.g., lead to development of an altered gait (i.e., walking technique), thus increasing the risk of falling.

In some preferred embodiments, the integrated ankle stabilizing can be made with any type of plastic or foam or any other appropriate material having strength and rigidity suitable for stabilization. In some embodiments, the support structure could include one or more hollow structure and a pump mechanism for feeding liquid or gas into the hollow structure for increasing the rigidity or support of the structure (e.g., employing an hydraulic or barometric pumping mechanism for, e.g., stabilizing the ankle against inversion and eversion). By way of example, such hydraulic or barometric pumping mechanisms can be configured similar to the NIKE PUMP™ as seen in U.S. Pat. No. 5,257,470 entitled Shoe Bladder System, the entire disclosure of which is incorporated herein by reference and/or similar to the bladder employed in U.S. Pat. No. 5,348,530 entitled Pneumatic Ankle Brace With Bladder and Pump Arrangement, the entire disclosure of which is also incorporated herein by reference.

In some preferred embodiments, the garment includes a sock portion that envelopes all or substantially all of the user's foot, including, preferably, all of the user's toes. In some preferred embodiments, the sock portion is adapted to provide warmth and to retain heat within the user's foot as a common sock.

In some embodiments, the sock can be made with any appropriate knit material, including, by way of example and not limitation cotton, wool, bamboo, nylon, etc. or any combination of materials that is used for making of socks.

In some preferred embodiments, the support structure includes a plastic brace that is integrally attached to the knit material of the sock. In some preferred embodiments, the plastic is a semi-rigid material.

In some examples, the plastic brace can be integrally attached by:
1) Sewing the plastic brace within a compartment or pocket inside the sock (e.g., preferably the compartment or pocket is formed with a similar soft material to the material of the sock such as to be comfortable against a user's foot);
2) Molding the plastic brace directly onto the sock (e.g., preferably on an outside of the garment so that the soft material of the garment is in contact with the user's foot); and/or
3) By employing other attachment mechanisms, such as, e.g., adhesives, staples, or other mechanisms.

In some preferred embodiments, the sock is placed over the end of a user's foot in the same manner of a common sock—e.g., the user's toes are placed into the open end of the sock and the sock is slid over the user's foot. In some preferred embodiments, the sock is elastically stretchable such as to stretch over the user's foot until the user's foot is fully inserted into the sock. In some embodiments, the sock can include one or more zipper along a side thereof to facilitate placement over the user's foot. In some examples, such a zipper can be along a front, back and/or either lateral side of the sock.

In some embodiments, the sock can be further secured after insertion of a user's foot by the addition of one or more support straps, such as, e.g., a VELCRO™ support strap (i.e., a support strap having an adjustable hook and loop attachment), an elastic band and/or the like. In this regard, any appropriate hook and loop strap mechanism can be employed, such as, e.g., employing hook and loop attachment straps similar to any of the structures in the following patents, the entire contents of which are incorporated herein by reference: U.S. Pat. No. 4,411,077, entitled Athletic Shoe with Attached Ankle Brace; U.S. Pat. No. 4,495,942, entitled Dynamic Ankle Brace.

In some embodiments, in addition to providing stabilizing support for the user, the garment can be configured to provide a desired level of compression, or can be adapted to vary the compression, and/or can be adapted to provide a graduated compression (e.g., varied level of compression along the height of the sock) in order to address issues related to, e.g., swelling in the lower extremities, etc. In some embodiments, the degree of compression of the sock can be selected as very light, light, moderate, high or extra high (see, e.g., illustrative ranges below). In some embodiments, upon the user's placement of the sock on the user's lower extremity (e.g., foot and ankle), the garment will provide a level of compression based on the elasticity of the sock portion. Towards that end, some embodiments can be configured to provide a very light compression, while others could be configured to provide a light compression, while others could be configured to provide a moderate compression, while others could be configured to provide a high compression, while others could be configured to provide an extra high level of compression. Moreover, as indicated above, some embodiments could be configured to provide a graduated compression along the height of the sock. For reference, see the chart below outlining illustrative compression levels in mm Hg.

| Level of Compression | Standard (mmHg) |
| --- | --- |
| Very light | About 5-14 |
| Light | About 14-20 |
| Moderate | About 21-30 |
| High | About 31-40 |
| Extra High | About 41-60 or more |

In some of the preferred embodiments, in addition to this level of compression, the garment can include straps that can be tightened which can achieve higher localized compression in regions of the straps and provide further support.

It should also be appreciated that many embodiments would not employ compression. For example, some preferred embodiments would actually not include compression, such as, e.g., if the garment is desired to be worn in bed during resting, as compression is not desirable for use while resting.

In some embodiments, the garment is to have an integrated orthotic member for underneath a user's foot within the sock. In some embodiments the orthotic member can include an arched central region serving as an arch support (see, e.g., example discussed above). In addition, in some embodiments the integrated orthotic member can include a posted heel to further aid in the stabilization of the user's lower extremity and reduce the risk of falling. In some examples, the posted heel can be either intrinsically or extrinsically formed. In this regard, a posted heel involves the addition of external material added to the heel area of the orthotic. This can be extrinsically formed by adding material to the orthotic or intrinsically formed by altering the shape of the orthotic itself based on the cast forming the orthotic.

According to some preferred embodiments, a main purpose of the device is to provide a sock-like lower extremity garment that is configured to support a user's foot and ankle in order to reduce the risk of falling—i.e., to serve as a "sock brace." While in some embodiments, the device can employ compression (as discussed above), in some preferred embodiments compression can be omitted. According to some preferred embodiments, a sock brace is provided that includes the following components within a foot-enveloping sock:
1) An arch support;
2) High medial and lateral flanges to reduce inversion/eversion at the sub-talar joint, to reduce the risk of one's ankle "giving out;"
3) A deep heel cup for the foot portion (to stabilize one's heel);

4) A semi-rigid design for the brace to allow some range of motion at one's ankle, which is helpful with proprioception; and 5) A layer of padding under one's foot for, e.g., shock absorption accommodate for calluses and other pressure points) and, thus, reduce pain on ambulation.

With respect to the inclusion of an "arch support," the arch support feature is preferably a raised, arcuate central region that is provided to support the arches in the foot. There are many bones, joints, ligaments and tendons in the foot. People with arthritis, tendinitis, plantar fasciitis, bunions, hammertoes, etc., all benefit from arch support in their shoes when ambulating. In the preferred embodiments, arch support is incorporated into a sock brace garment so that, e.g., the elderly are able to ambulate with a little less pain and without the need to put on their shoes or for their shoes to have arch supports added. Arch supports help re-align the bones/joints in the foot, support all of the joints in the mid-foot, reduce tension on top of the foot that comes from weight-bearing and, thus, reduce pain.

Preferably, such an arch support includes an arcuate, raised central portion that is raised upward higher than a forward portion (i.e., under the fore part of the foot) and raised upward higher than a rearward portion (i.e., under the rear part of the foot). Moreover, the arch support is preferably proximate a medial side of the garment, and preferably has a greater height at a medial side than towards a lateral side of the device. In some embodiments, a peak height of the raised arch is at least a few millimeters above the forward and rearward portions, and in some preferred embodiments, it is at least 5 mm above the forward and rearward portions, and in some preferred embodiments, it is at least 10 mm above the forward and rearward portions, and in some other preferred embodiments, it is at least 15 mm above the forward and rearward portions.

With respect to the inclusion of "high medial and lateral flanges," these flanges help to reduce inversion/eversion at the sub-talar joint, to reduce the risk of one's ankle "giving out." For example, people that repeatedly sprain their ankles can face a condition in which their ankles are unstable. Similarly, the elderly can develop ankle instability due to the aging process which can essentially make their ankles unstable. High medial and lateral flanges are formed by raised borders of the orthotic/arch support on the medial and lateral sides of the device. In the preferred embodiments, these medial and lateral flanges are raised a height sufficient to effectively locate or fix the user's foot in a certain position on the device. Otherwise, the user's foot could, e.g., slide off the side of the device during use. In some illustrative embodiments, the medial and lateral flanges are raised in a manner to extend upwardly at least about 3 mm, and in some other embodiments, the medial and lateral flanges extend upwardly at least about 5 mm, and in some embodiments, the medial and lateral flanges extend upwardly at least about 10 mm. Preferably, the flanges do not extend upwardly so high as to cause the device to be unduly rigid or to be difficult to place within a shoe or the like during use.

With respect to the inclusion of a "deep heel cup," a deep heel cup can, e.g., help stabilize one's foot by aligning one's feet with one's ankles, knees, and hips. In this manner, a proper foot alignment will help to, e.g., counter overpronation and supination, thereby reducing pain in one's feet, etc. In some illustrative embodiments, a deep heel cup includes a curved support surface to support the heel of a user, and raised edges. In some illustrative embodiments, a deep heel cup extends upwardly at least about 10 mm, and in some illustrative embodiments, the deep heel cup extends upwardly at least about 15 mm, and in some illustrative embodiments, the deep heel cup extends upwardly at least about 20 mm. In some illustrative embodiments, the deep heel cup extends upwardly around the entire rear of the user's heel from medial to lateral sides around the back of the heel.

In some illustrative embodiments, heel cup, flanges and/or arch support features of one or more of the below patents can be employed, the entire disclosures of which are incorporated herein by reference as though recited herein in full:
1. U.S. Pat. No. 9,131,746;
2. U.S. Pat. No. 9,072,339;
3. U.S. Pat. No. 7,694,437;
4. U.S. Pat. No. 6,601,320;
5. U.S. Pat. No. 6,315,786;
6. U.S. Pat. No. 6,269,555;
7. U.S. Pat. No. 6,125,557;
8. U.S. Pat. No. 6,101,655;
9. U.S. Pat. No. 6,038,793;
10. U.S. Pat. No. 5,713,143;
11. U.S. Pat. No. 4,791,736.

With respect to the "semi-rigid design" of the preferred embodiments, as indicated above the preferred embodiments preferably allow for some range of motion at the ankle, which is helpful with proprioception. In contrast to a rigid ankle foot orthosis (AFO), which blocks motion around the ankle and foot completely, thus preventing motion at any joints, the preferred embodiments do not employ such a rigid design or structure.

In the preferred embodiments, a semi-rigid design is provided that allows the user's ankle to move up and down with only slight restriction, so it can stabilize the foot and ankle, but not completely prevent motion. Thus, in the preferred embodiments, a semi-rigid structure is provided that allows the user's ankle to move, as opposed to a rigid device that completely blocks ankle range of motion (ROM).

With respect to the "layer of padding" under one's foot, in the preferred embodiments, the sock brace garment is configured to include a layer of padding extending underneath the entire bottom surface of a user's foot. In some preferred embodiments, the padding is not so deep as to cause instability, but helps to alleviate pressure on the foot. In some embodiments, the layer of padding is relatively thin, such as, e.g., about a few millimeters, such as, e.g., 1 to 3 millimeters thick.

In some embodiments, the layer of padding can be of a similar construction to insoles used for diabetes, arthritis, and otherwise sensitive feet that are designed primarily to alleviate pressure on the foot, absorb impact shock, and minimize any abrasive rubbing or irritation against the skin of the foot. In some embodiments, the layer of padding can be made with a lightweight closed-cell elastomeric foam, or a thermoplastic foam, such as, e.g., PLASTAZOTE to help keep the product light, to assist in pressure relief, and to reduce skin shearing.

Exemplary Embodiments

The attached figures show some exemplary embodiments of the present invention discussed above.

Figure 1A:
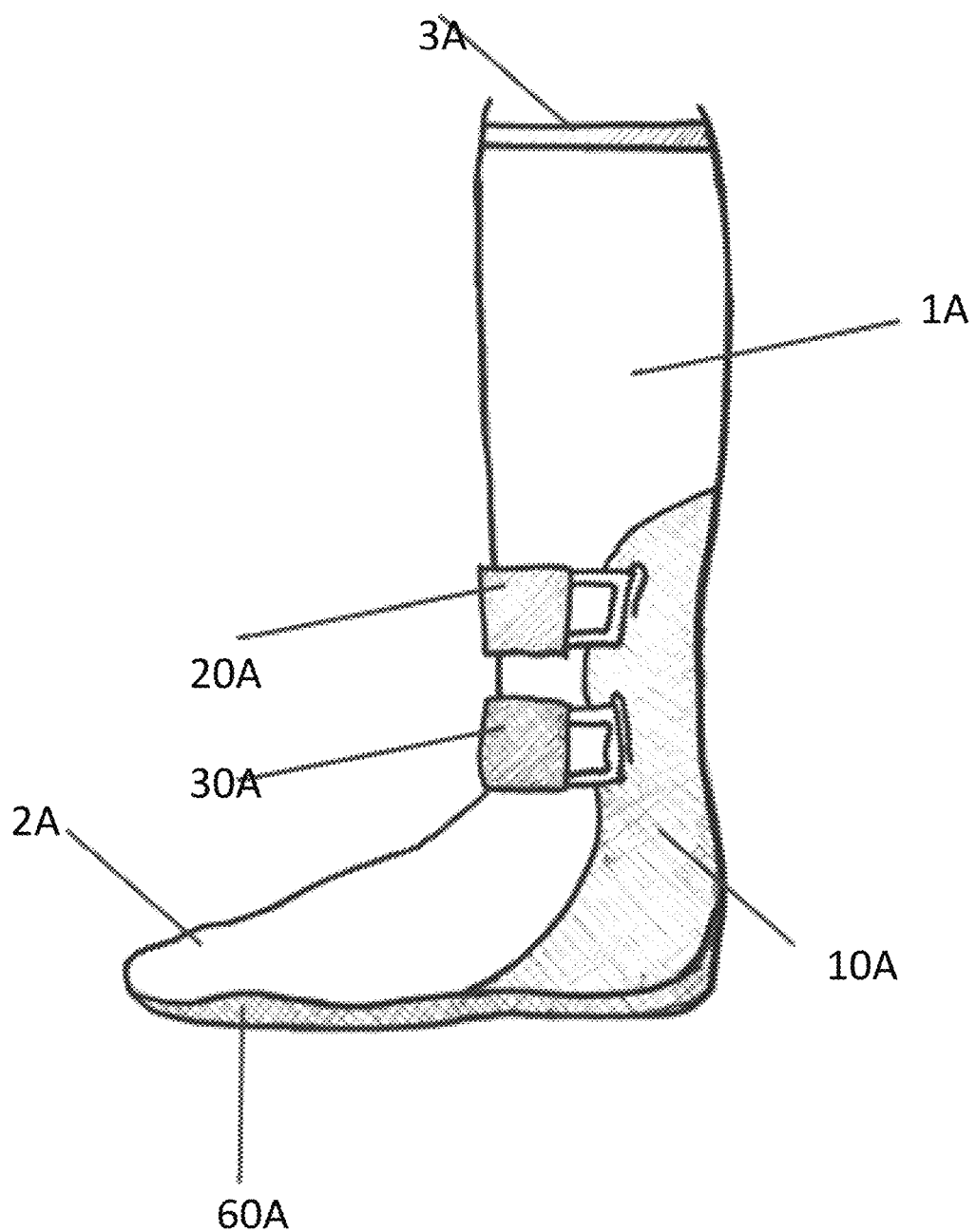
FIG. 1A is a left side view of an illustrative garment according to a first embodiment of the invention.
Figure 1B:
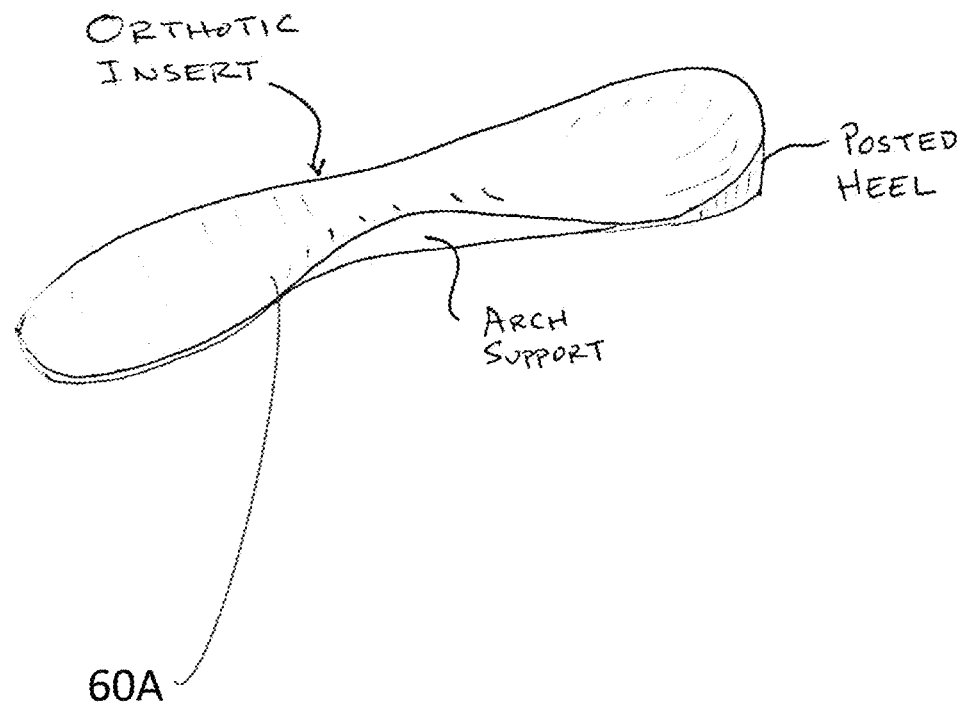
FIG. 1B is an elevational view of an illustrative orthotic portion integrated into a garment according to some preferred embodiments of the present invention.

Towards that end, FIGS. 1A and 1B show an illustrative first embodiment that includes a garment adapted to fit over a lower extremity (e.g., foot and ankle) having a sock portion 1A that fully envelopes the lower extremity of a user, including a toe section 2A that fully encloses the distal portion of a user's foot (e.g., toes) and an opening 3A. Here, the sock portion 1A can include materials and/or features as discussed above. In the illustrated embodiment, the sock portion is flexibly expandable in order to be stretched over a user's foot similar to a common sock. In this illustrated example, the garment includes three additional novel components that are integrally connected with the sock portion 1A.

First, the garment includes a support member 10A that is arranged as shown such as to extend up around a heel region of the user to a position above the user's ankle. In some preferred embodiments, the support member 10A is integrally attached to the sock (e.g., on the exterior of the sock), such as, e.g., by mechanical connection (e.g., sewing, rivets, staples, clips and/or the like), by adhesives, by molding thereto, by heat-bonding and/or by other known techniques.

Second, the garment includes a lower pad or orthotic portion 60A that spans across the entire lower surface of the sock such as to span across an entire sole of a user's foot during use. In preferred embodiments, the orthotic portion 60A can include a cushioned upper surface 60B facing the user's foot and some more rigid portions to provide, e.g., arch support and/or heel support. In some embodiments, e.g., the orthotic portion 60A can be structured similar to the example shown in FIG. 1B. In some preferred embodiments, the orthotic member 60A is integrally attached to the sock (e.g., on the exterior of the sock), such as, e.g., by mechanical connection (e.g., sewing, rivets, staples, clips and/or the like), by adhesives, by molding thereto, by heat-bonding and/or by other known techniques. In some embodiments, the orthotic member can be mounted inside the sock and another external member can be attached outside the sock (such as, e.g., a non-slip member), while in other embodiments the orthotic member can be mounted outside of the sock. In some embodiments a further non-slip member with high traction can be attached to the bottom of the orthotic or garment to facilitate walking during use.

Third, the garment can include one or more support straps, such as, e.g., two support straps 20A and 30A shown in the illustrated embodiment. In the preferred embodiments, the support straps attach to opposite sides of the support member 10, and extend around the front of the user's foot, in order to provide enhanced support. In the preferred embodiments, the user can select a desired degree of tightness of the straps. As discussed above, any type of strap attachment can be employed, such as, e.g., VELCRO or other desired attachment.

Although FIG. 1A shows one side of the garment, it is to be understood that the garment in this embodiment is preferably substantially symmetrical in configuration. Accordingly, the opposite side would preferably have a similar, but reversed, structure.

Figure 2:
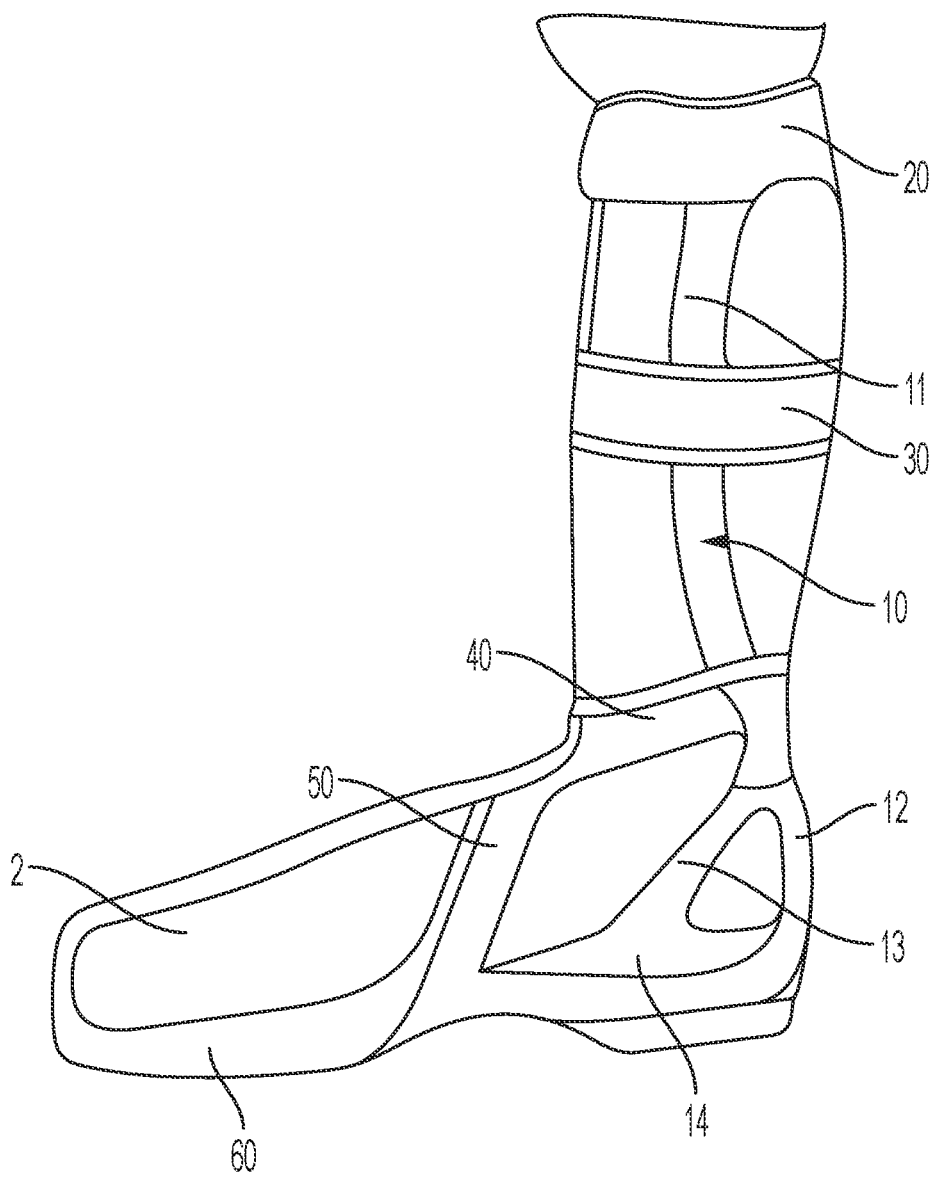
FIG. 2 is a left side view of an illustrative garment according to a second embodiment of the invention.
Figure 3:
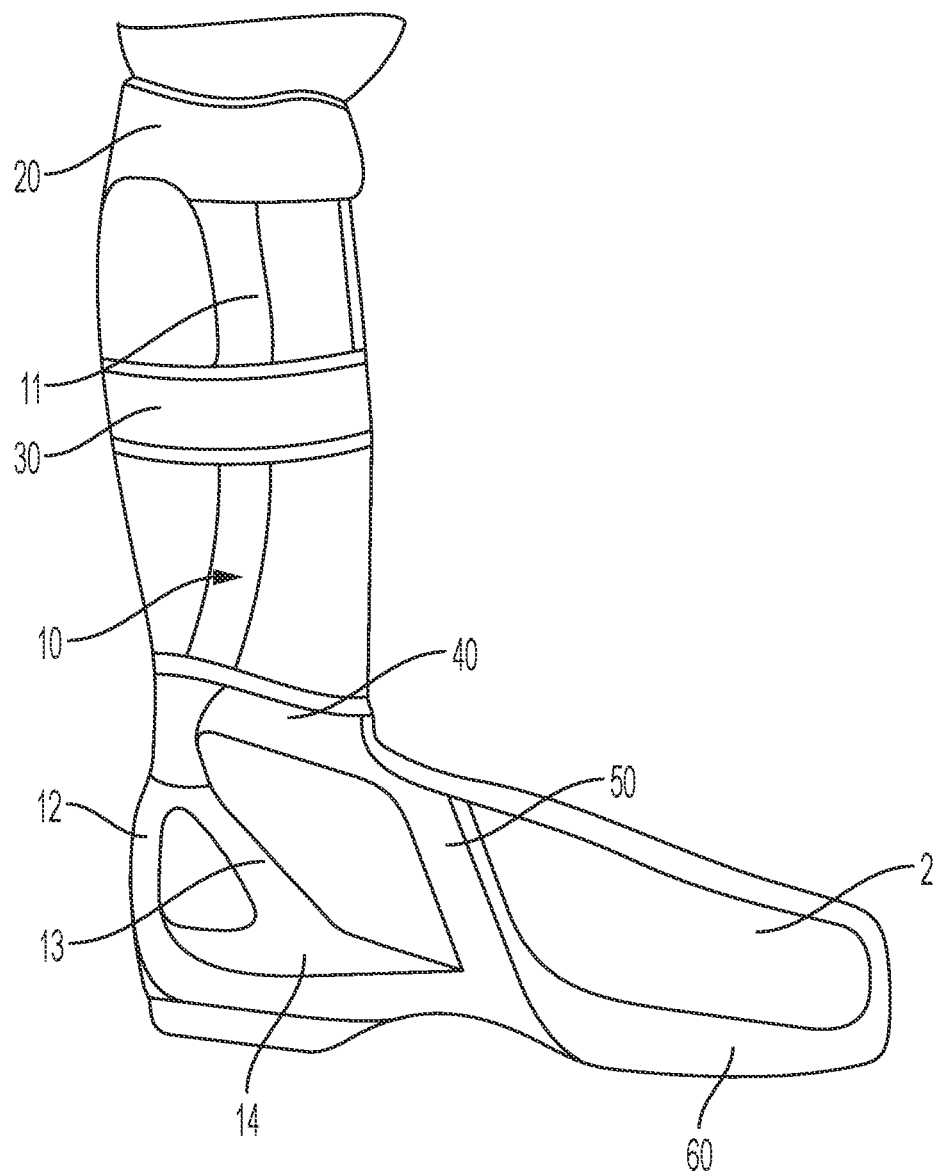
FIG. 3 is a right side view of the illustrative garment according to the second embodiment of the invention shown in FIG. 2.

FIGS. 2 and 3 illustrate a second exemplary embodiment of the invention. In this illustrative example, a garment is provided that is similarly adapted to fit over a lower extremity (e.g., foot and ankle) having a sock portion that fully envelopes the lower extremity of a user, including a toe section 2 that fully encloses the distal portion of a user's foot (e.g., toes) and an opening similar for insertion of one's foot. Once again, the sock portion can include materials and/or features as discussed above. In the illustrated embodiment, once again, the sock portion is flexibly expandable in order to be stretched over a user's foot as a common sock. In this illustrated example, as with the first embodiment, the garment includes additional novel components that are integrally connected with the sock portion.

First, similarly to the first embodiment, the garment includes a support member 10 that is modified from the support member 10 of the first embodiment. In particular, the support member 10 includes open areas that create a semi-FIG. 8 structure (i.e., when viewed from the rear), including a lower rear opening proximate the user's heel and an upper rear opening extending at a location above the malleolus/ankle). More specifically, the support member includes an upper later portion that curves from a top side of the garment near the opening into the sock and extends laterally along the sock and then to a rearward portion of the sock proximate the location of a user's ankle, the support member also includes a rear heel cup portion 12 that extends around the rear of the heel area, and also includes a lateral side portion 13 that extends downward toward a base of the garment. In some embodiments, the lateral side portion 13 can extend to an arch support portion 14. In some embodiments, the arch support portion 14 can be integrated as part of an orthotic, or as part of a lower pad member 60. In some embodiments, the lower pad member 60 can be an orthotic and in some embodiments, the member 60 can include a non-slip material attached thereto similar to the first embodiment. In some preferred embodiments, the support member 10 is integrally attached to the sock (e.g., on the exterior of the sock), such as, e.g., by mechanical connection (e.g., sewing, rivets, staples, clips and/or the like), by adhesives, by molding thereto, by heat-bonding and/or by other known techniques.

Second, with respect to the lower pad or orthotic portion 60, the portion preferably spans across the entire lower surface of the sock such as to span across an entire sole of a user's foot during use. In preferred embodiments, the orthotic portion 60 can include a cushioned upper surface facing the user's foot and some more rigid portions to provide, e.g., arch support and/or heel support. In some embodiments, e.g., the orthotic portion 60 can be structured similar to the example shown in FIG. 1B. In some preferred embodiments, the orthotic member 60 is integrally attached to the sock (e.g., on the exterior of the sock), such as, e.g., by mechanical connection (e.g., sewing, rivets, staples, clips and/or the like), by adhesives, by molding thereto, by heat-bonding and/or by other known techniques. In some embodiments, the orthotic member can be mounted inside the sock and another external member can be attached outside the sock (such as, e.g., a non-slip member), while in other embodiments the orthotic member can be mounted outside of the sock. In some embodiments a further non-slip member with high traction can be attached to the bottom of the orthotic or garment to facilitate walking during use.

Third, the garment can include one or more support straps, such as, e.g., four support straps 20, 30, 40 and 50 shown in the illustrated embodiment. In the preferred embodiments, the support straps 20, 30 and 40 attach to opposite sides of the support member 10, while the support strap 50 attaches to opposite sides of the orthotic portion 60 or arch support portion 14 and extend around the front of the user's foot, in order to provide enhanced support. In the preferred embodiments, the user can select a desired degree of tightness of the straps of one or more of the support straps 20, 30, 40 and/or 50. As discussed above, any type of strap attachment can be employed, such as, e.g., VELCRO or other desired attachment. In the most preferred embodiments, at least the straps 20 and 30 are adjustable in this manner with, e.g., VELCRO or the like adjustable straps.

As with the first embodiment, the garment in this second embodiment is preferably substantially symmetrical in configuration. Accordingly, the opposite side preferably has a similar, but reversed, structure, such as, e.g., illustrated in FIG. 3.

Figure 4:
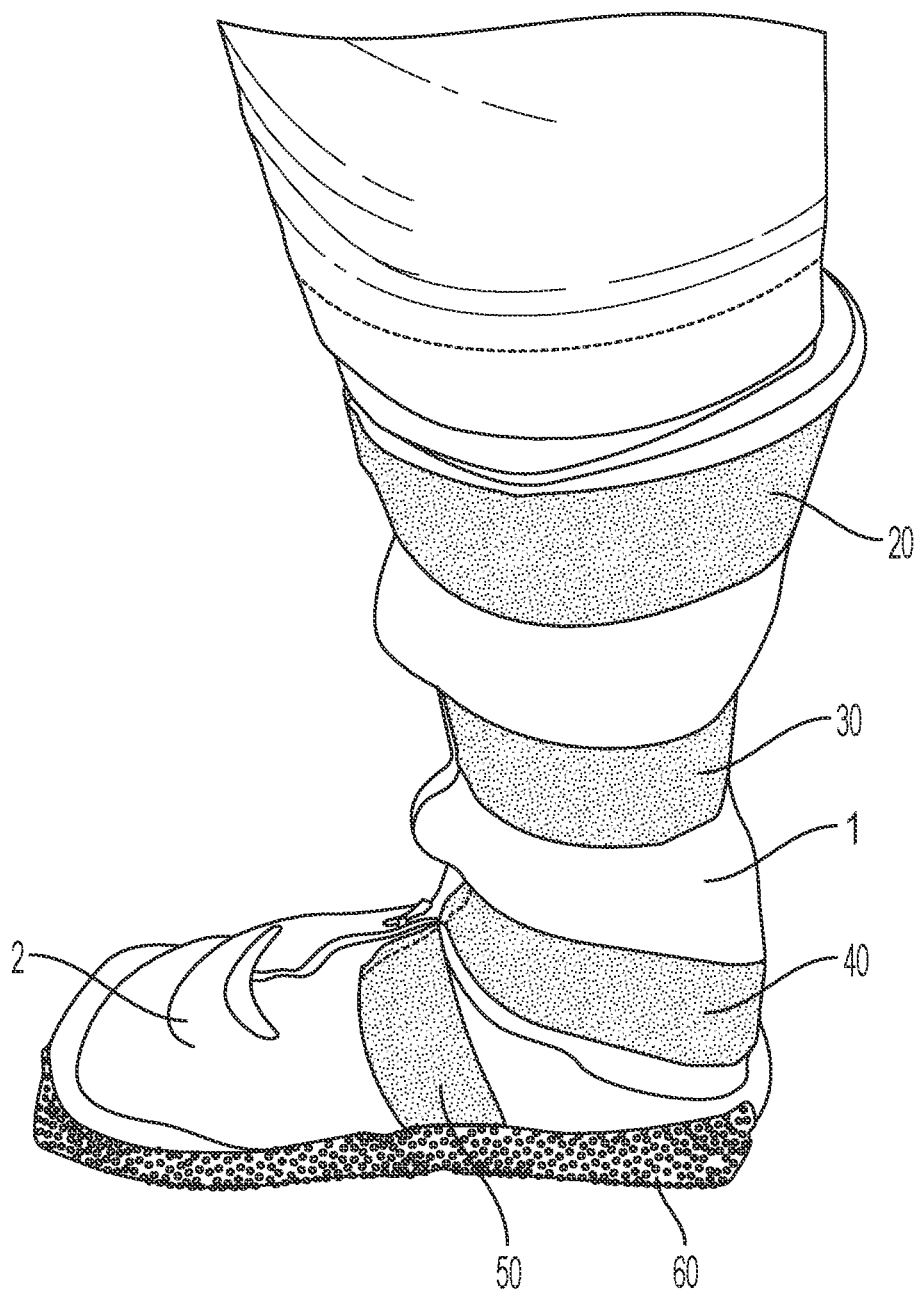
FIG. 4 is an elevational left side view of an illustrative garment according to a third embodiment in a state of being worn by a user.
Figure 5:
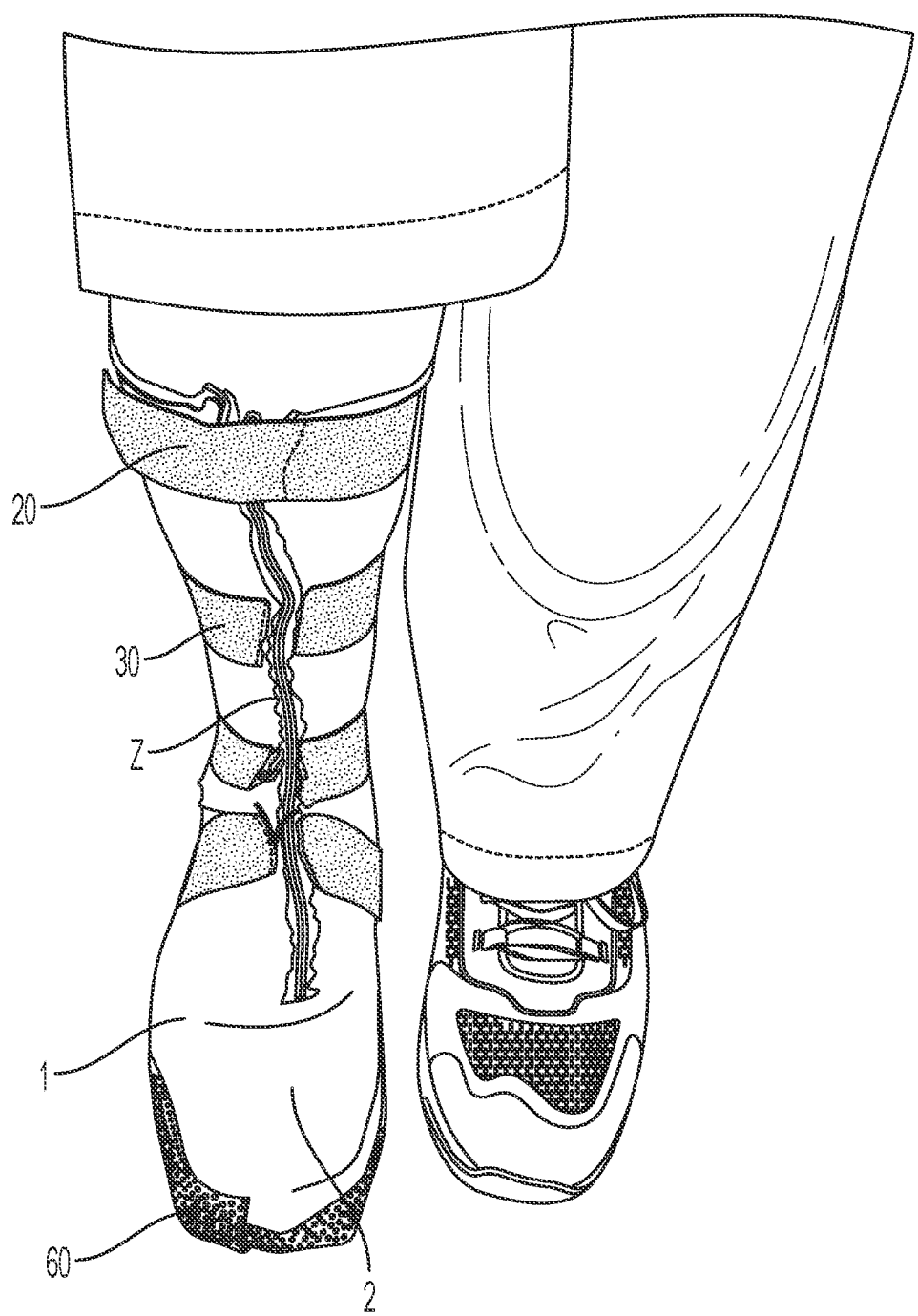
FIG. 5 is an elevational front view of the illustrative garment according to the third embodiment shown in FIG. 4 in a state of being worn by a user.

FIGS. 4 and 5 illustrate a third exemplary embodiment of the invention. The embodiment shown in FIGS. 4 and 5 is similar to the second embodiment and includes a similar flexible sock portion 1 that encompasses the entire lower extremity of the user, a similar lower pad or orthotic portion 60, and similar support straps 20, 30, 40 and 50.

As best seen in the front view shown in FIG. 5, in this third embodiment, the sock portion 1 includes a zipper Z that extends from the top opening of the sock portion to the dorsum pedis or instep (i.e., top of the foot). In this manner, the sock portion 1 can be readily placed over the user's lower extremity with the zipper Z in an open position, and, once, inserted, the zipper Z can be "zipped up" to a fully closed position. FIG. 5 illustrates the zipper Z in such a fully closed position.

As also shown in FIG. 5, in this illustrative embodiment, the straps 30, 40 and 50 are preferably elastic straps that provide increased support once the zipper is in the fully closed position. However, the straps 30, 40 and 50, in this example, are not adjustable. In this example, the strap 20 preferably includes an adjustable VELCRO connection whereby the upper end of the garment can be adjustably fitted by repositioning of a strap end with the VELCRO connection.

In the embodiment shown in FIGS. 4-5, the garment includes a support 10 that is similar to the support 10 of the second embodiment. However, in the embodiment shown in FIGS. 4-5, the support 10 is integrated inside the sock portion 1. In some preferred embodiments, the support is located within an internal pocket or pouch as discussed above. As also discussed above, the support 10 is preferably integrally attached to the sock portion 1.

In some preferred implementations of the first through third embodiments discussed above, the garment can be more particularly configured as discussed below in relation to FIGS. 6 and 7.

First, in some implementations, as shown in FIG. 6, the height of the top of the garment can be selected to extend up to a location D within a range of below a user's knee to above a user's ankle. In some preferred embodiments, the sock will extend up to a height D that is above a bottom portion of the gastrocnemius muscle in the calf of the user. In some preferred embodiments, the sock will extend up to a height D that is above a widest portion of the user's calf in the region of the gastrocnemius muscle. Notably, in contrast to many ankle braces that extend just above the ankle, some preferred embodiments of the present invention extend higher up the leg (e.g., to about the widest portion of the calf or up near the knee) to, e.g., increase stability.

Figure 7:
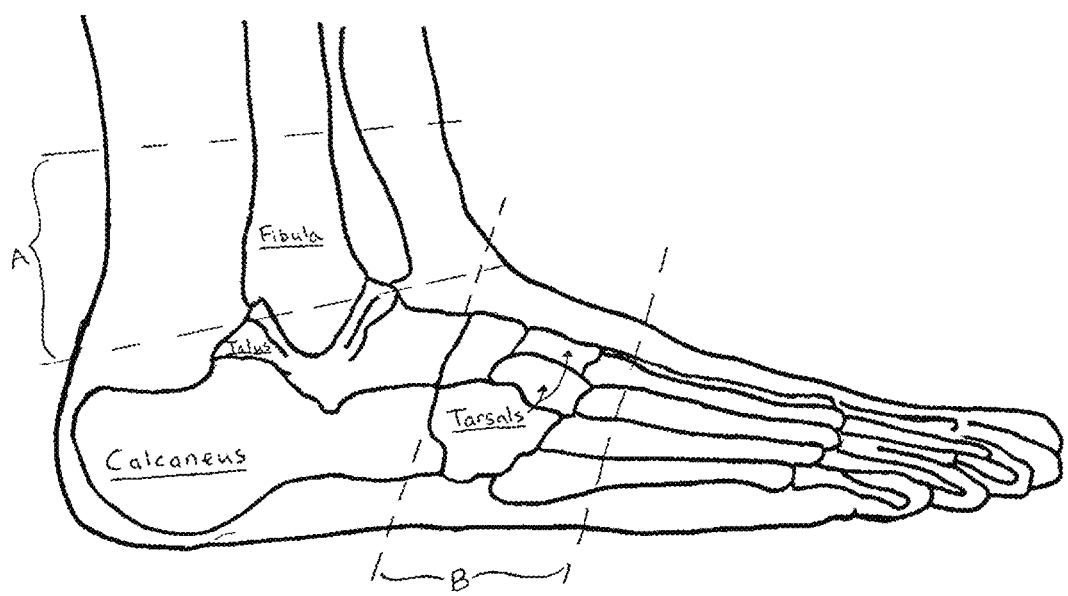

Second, in some implementations, as shown in FIG. 7, the support 10 or 10A preferably extends around the rear portion of the user's lower extremity from approximately the location of the fibula and back to the rear of the user's lower leg surrounding the Achilles tendon. In some preferred embodiments, the support 10 or 10A will extend forwardly enough to overlap the fibula on both lateral sides for enhanced support.

Third, in some implementations, as shown in FIG. 7, the strap 40 is preferably located at least partly (or in some embodiments fully) within a region A at or proximate a lower end of the fibula, and the strap 50 is preferably located at least partly (or in some embodiments fully) within a region B at or proximate the tarsals of the user's foot as shown. As also shown, the strap 30 is preferably located substantially above the region A above the user's ankle.

As described above, in the preferred embodiments, a garment is provided that includes a common sock portion that fully or substantially envelopes a user's foot or the like, along with a support 10/10A that provides, e.g., lateral ankle support, along with a foot pad or orthotic 60 that provides, e.g., arch support, and, by connection of the support 10/10A with the foot pad or orthotic 60, the garment also provides enhances support. In some preferred embodiments, the support of the garment is also configured to provide "dorsal assist" of the user's foot in a frontal plane (e.g., to inhibit falling downward of the toe in the direction of the downward arrow df shown in FIG. 6 for some persons with compromised dorsal stability).

As a result, the preferred embodiments provide a comfortable sock-like article that achieves substantial benefits and advantages.

In some preferred embodiments, the garment is constructed such as to be machine washable as a single integrated unit, which the sock portion and the support portion and the lower pad or orthotic portion combined. In some alternative embodiments, the support portion and the orthotic portion can be separated for washing of the sock portion. For example, the support portion and the orthotic portion can be configured to be placed within pouches or pockets in the socket and removed for washing and care of the garment.

In some preferred embodiments, the garment is constructed such that the garment is not bulky and such that, like a common sock, can be worn within a common shoe, sneaker, boot or other footwear. By way of example, in some embodiments, the thickness of the garment around the lateral sides of the user's foot is not more than about 4.5 mm, and in some more preferred embodiments, is not more than about 4.0 mm, and in some even more preferred embodiments, is not more than about 3.5 mm, and in some even more preferred embodiments, is not more than about 3.0 mm, and in some even more preferred embodiments, is not more than about 2.5 mm, and in some even more preferred embodiments, is not more than about 2.0 mm. In the preferred embodiments, this minimal thickness pertains to the entire thickness of the garment above the bottom of the garment (i.e., the bottom containing the bottom pad or orthotic).

In some embodiments, the thickness of the bottom pad or orthotic portion can have a greater thickness, but is preferably sized to fit within a common shoe similar to a common orthotic.

In this manner, the garment can preferably be worn and used similar to a common sock, providing all the common advantages and uses and functions of a common sock, and handled similar to a common sock (e.g., for washing and care of the garment), while providing advanced benefits and functions as described herein above.

In contrast to many existing braces or supports, the present garment is configured to be worn similar to a pair of socks, such as to, e.g., be comfortably worn around a house or dwelling, while concurrently providing enhanced stability and other benefits as described above. While many ankle or foot products do not provide any eversion or inversion or other stability until used in conjunction with a shoe or other footwear, the preferred embodiments of the present invention provide such benefits by the garment alone. As many elderly or otherwise ailing persons spend much of their time indoors, in nursing homes, hospitals and/or other facilities, the present invention provides a garment that can readily be worn indoors alone without other shoes or structures while providing great advantages in relation to stabilization, etc., as discussed above, along with warmth and comfort, etc.

Figure 8A:
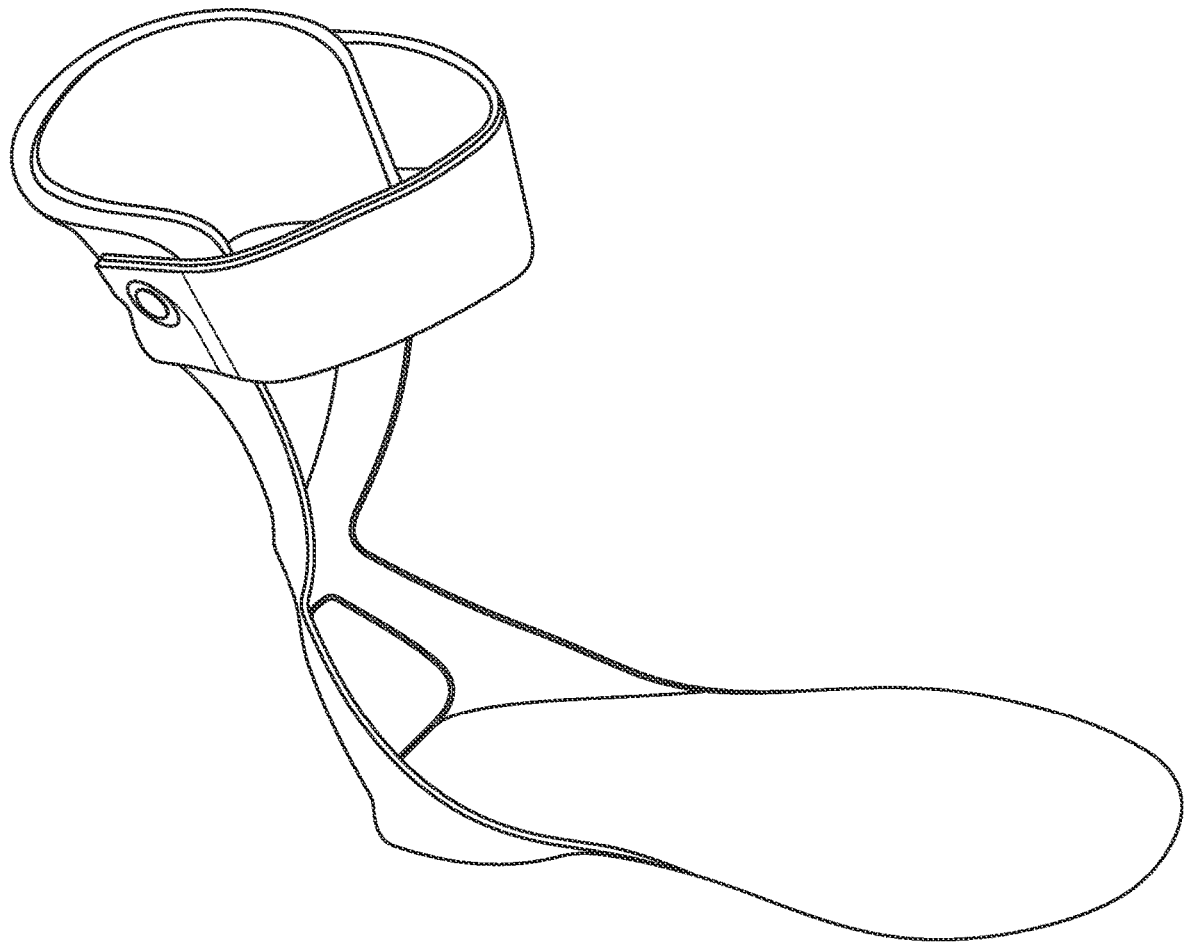
Figure 8B:
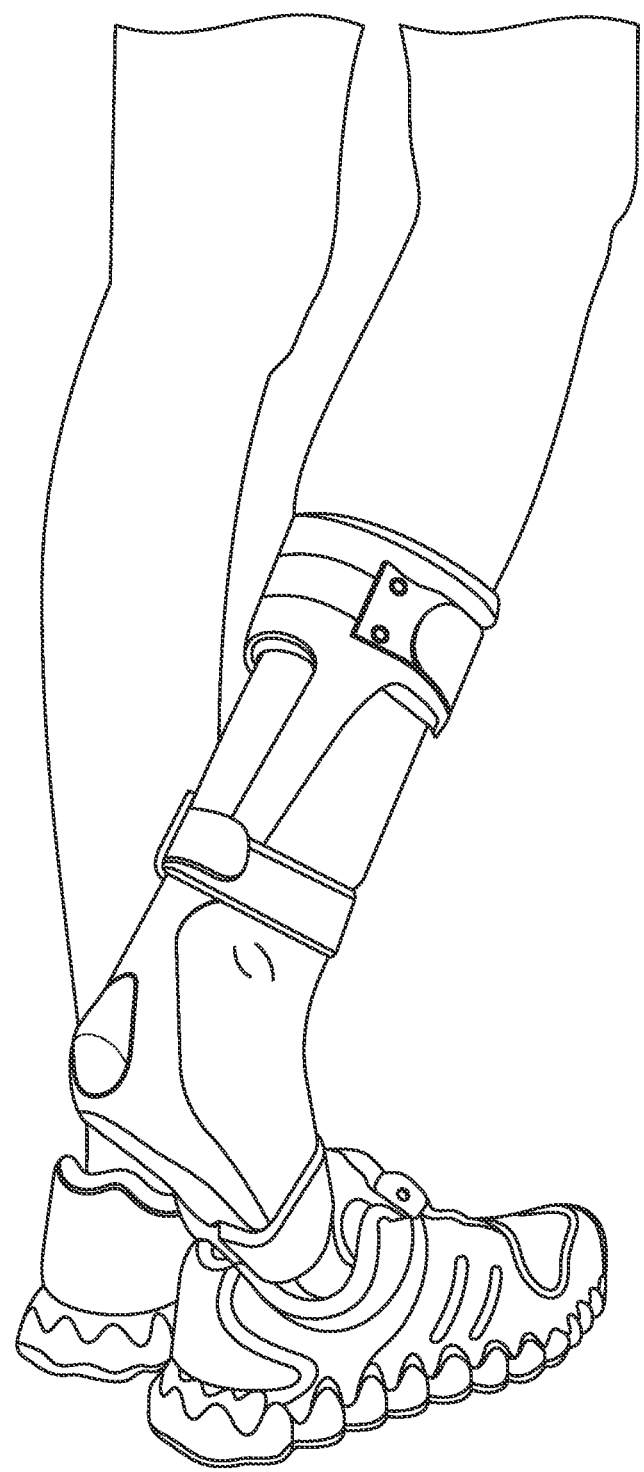

In some embodiments, an existing support structure of the type shown in FIG. 8A or 8B can be employed which is integrated within a garment. In some preferred embodiments, this structure shown in FIG. 8A or 8B is modified to have structure as described in the above embodiments.

In some embodiments, the support structure in the garment can involve a "double upright" structure in which upwardly extended supports extend along each side of the ankle (e.g., lateral and medial sides of the ankle) as long as the support is configured to lock the heel (e.g., with heel cup or the like). As one illustrative and non-limiting example, an existing support structure similar to that shown in FIG. 8D can be employed in some embodiments, which is preferably modified to lock the heel as discussed above.

In some other illustrative and non-limiting embodiments, the support structure in the garment can involve a structure that comes around the front of the ankle similar to, in an illustrative case, the example shown in FIGS. 8C(1) and 8C(2) as long as the support is configured to lock the heel (e.g., with heel cup or the like).

In the existing structures shown in FIGS. 8A to 8D, it should be appreciated that such existing structures do not teach or suggest features of the more preferred embodiments, such as, e.g., integration within a garment as well as preferred structural features of the support.

With respect to FIG. 8A, this figure shows an illustrative existing structure of ProCare. See: https://www.sourceortho.net/super-lite-afo-brace/ (ProCare Super-Lite AFO Leaf Spring "Provides lateral support for those with extreme weakening of the foot and ankle joints, while adding stationary rear leg support. The Super-Lite ProCare AFO is fabricated by injection-molded polyethylene and provides static dorsiflexion assistance and lateral stability for the entire foot-ankle area. The slim design of the AFO aligns with the sculpted ankle helps to prevent contact with bony protrusions (malleolus). This drop foot brace model provides for a minimal to full range of motion and is lighter than a traditional solid heel AFO splint making this foot drop brace an excellent choice." . . . "The Procare Super-Lite AFO injection molding allows for thicker polyethylene on the vertical aspect for rigidity and a thinner footplate. It can be trimmed and molded via heat gun for a tailored fit. The low arch and open heel give this splint a streamlined profile that fits easily into many shoes." "Available in either a right or left, mens (larger foot plate/heel) and women sizes (shorter foot plate/narrower heel)."

With respect to FIG. 8B, this figure shows another illustrative existing structure involving an ankle foot orthosis AFO Swedish LSO drop foot leg brace. See: http://www.ebay.com/itm/ANKLE-FOOT-ORTHOSIS-AFO-SWEDISH-LSO-DROP-FOOT-LEG-BRACE-/332200831927?var=&hash=item4d58b66bb7.

With respect to FIGS. 8C(1) and 8C(2), these figures show another illustrative existing structure showing an Ossur AFO dynamic foot drop brace. See: http://e-medicalbroker.com/product-eng-4862-Ossur-AFO-R-dynamic-foot-drop-brace.html.

Figure 8D:
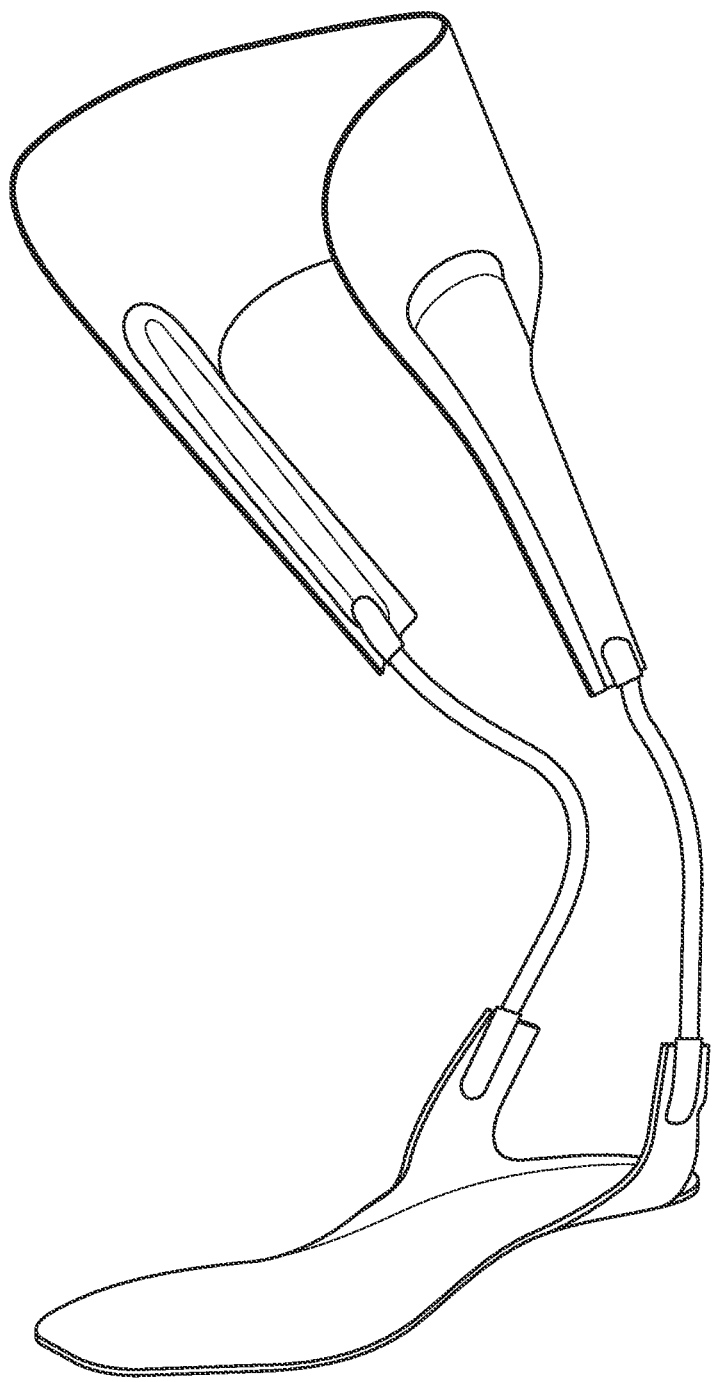

With respect to FIG. 8D, this figure shows another illustrative existing structure showing a Centri Dynamic Walk Standard device. See: http://e-medicalbroker.com/product-eng-4817-Centri-Dynamic-Walk-Standard.html.

Although these background structures shown in FIGS. 8A-8D do not teach or show substantial aspects of the present invention, in some embodiments aspects of these background brace structures can be employed in embodiments of the present invention. For example, these background devices can be modified to include deep heel cups, lateral and medial flanges, and arch supports in some embodiments, and also to be integrated within a sock garment in some illustrative embodiments.

Figure 9:
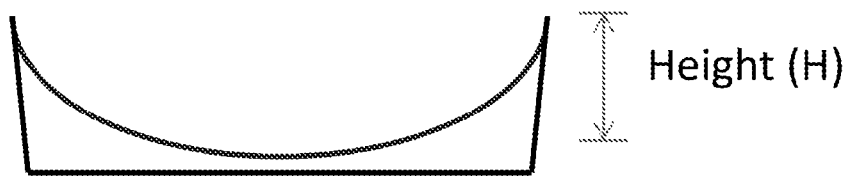
FIG. 9 is a cross-sectional rear view showing an illustrative deep heel cup section according to some illustrative embodiments.

For further illustration, FIG. 9 shows an illustrative cross-sectional rear view of an illustrative deep heel cup section of an orthotic portion of the device in some embodiments. As shown in this illustrative embodiment, the heel support portion includes an arcuate heel supporting surface and a generally flatter lower ground pressing surface. In addition, as illustrated, the deep heel cup can extend up a height H in some embodiments (see discussion above).

Figure 10:
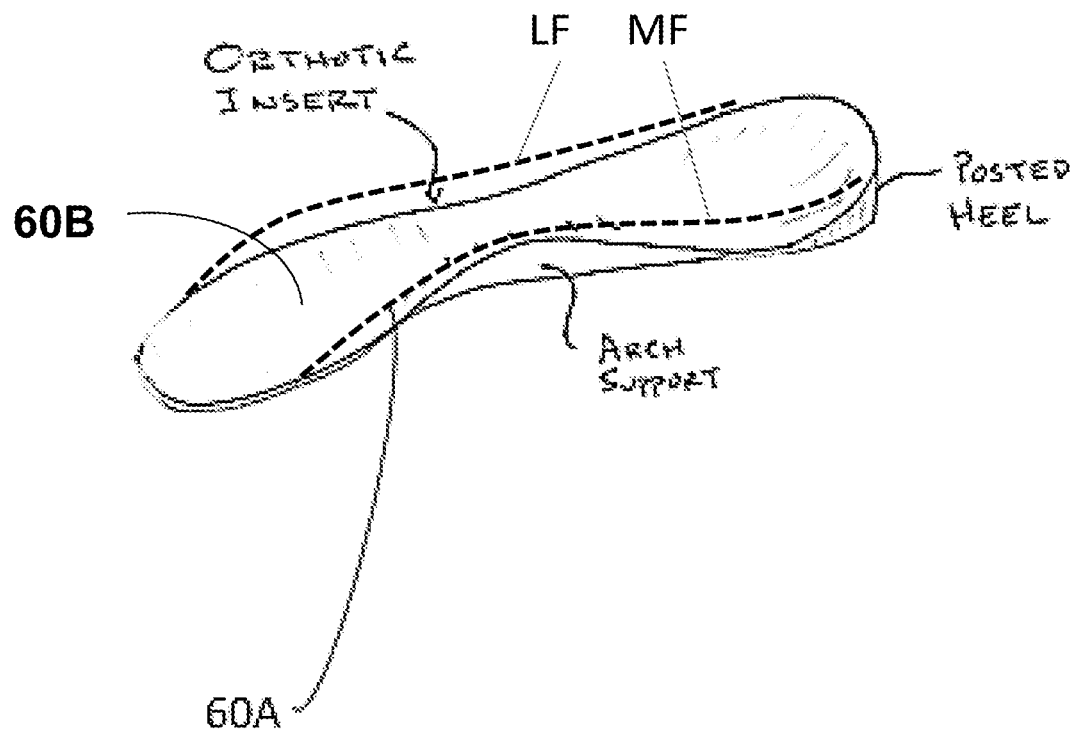
FIG. 10 is an illustrative elevational view of an illustrative orthotic portion similar to that shown in FIG. 1B with illustrative medial and lateral support flanges.

For further illustration, FIG. 10 shows an illustrative medial flange MF and an illustrative lateral flange LF in some illustrative embodiments. As illustrated, the flanges can extend upwardly along some or all of the medial and lateral sides of the orthotic portion (see discussion above).

Figure 11:
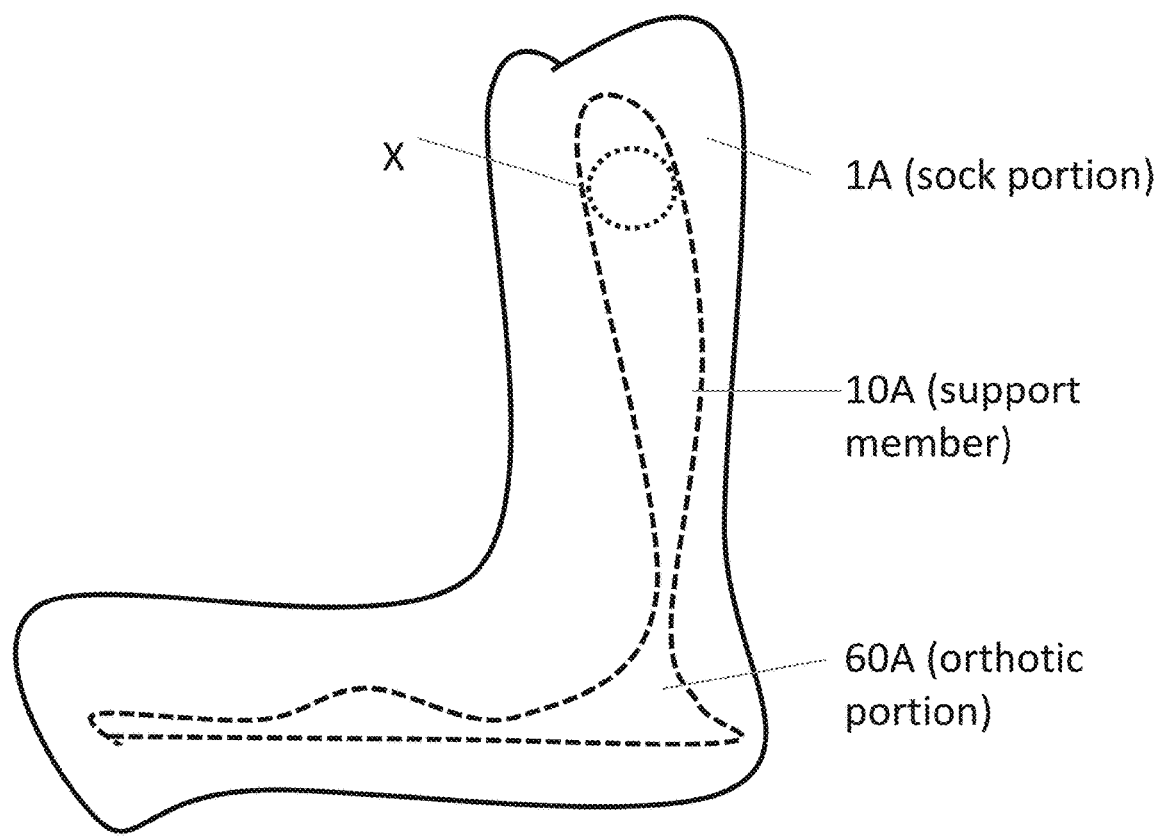
FIG. 11 is a schematic diagram showing a support member integrated with a sock portion according to some illustrative embodiments.
Figure 12:
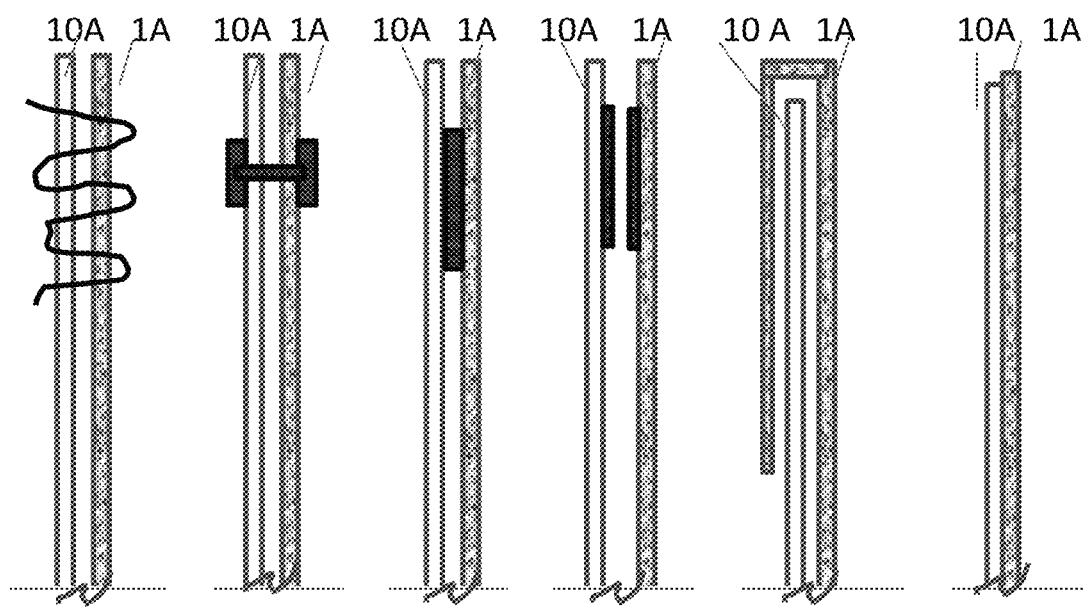
FIG. 12 is a schematic diagram showing portions of a plurality of top regions of illustrative lower extremity garments with sock portions integrated with support members using a plurality of different attachment mechanisms.

For further illustration, FIG. 11 shows an illustrative lower extremity garment according to some illustrative embodiments with a sock portion 1A surrounding an internal member having a support member 10A with an integral orthotic portion 60A. In some preferred embodiments, the garment is constructed as a unitary structure with the support member 10A integrally attached to the sock (e.g., on the exterior of the sock in some embodiments or on the interior of the sock in other embodiments), such as, e.g., by mechanical connection (e.g., sewing, rivets, staples, clips and/or the like), by adhesives, by molding thereto, by heat-bonding and/or by other known techniques. In some embodiments, the support member 10A and orthotic portion 60A are integrated inside of the sock portion 1A, with the support member 10A attached to the sock portion 1A at a region X proximate an upper end of the support member. For reference, FIG. 12 shows portions of upper regions of illustrative lower extremity garments showing a layer of fabric of a sock portion 1A adjacent a support member 10A in an area of regions X to show illustrative variations in integrating the support member 10A and the sock portion 1A in some embodiments. For example, a leftmost example shows the support member 10A attached to the sock portion 1A by threads T. A next adjacent example shows the support member 10A attached to the docket portion 1A by rivots R. A next adjacent example shows the support member 10A attached to the docket portion 1A by adhesive A. A next adjacent example shows the support member 10A attached to the docket portion 1A by hook and loop fastening fabric members attached to each element V (aka VELCRO). A next adjacent example shows the support member 10A attached to the docket portion 1A by insertion of a top end of the support member 10A inside an overhanging pocket of the sock portion 1A. For example, the sock portion 1A can be stretched upward such that the top of the support member 10A is received inside the pocket and the resiliency of the sock portion causes the sock member to retract and thus contain the support member 10A. A next adjacent example at the rightmost side of the figure shows the support member 10A attached to the docket portion 1A by fusing of the members together, such as, e.g., by heating or molding such that the support member (e.g., which can be a plastic or elastomeric material) melts and penetrates fabric of the sock portion such that upon cooling, the members are adhered together. While some embodiments have the support member 10A fixedly and non-removably attached to the sock portion 1A, in some preferred embodiments, the members are separable to facilitate washing, or repair or the like. For example, employing of releasable clips that are mounted on the support member 10A that releasably attach to the sock portion 1A or the embodiments such as wherein the support member 10A is removably located within a pocket in the socket during use can facilitate separation of the members in some embodiments.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. A lower extremity garment, comprising:
    a) a flexible sock configured to surround at least a user's foot and ankle, said flexible sock having a substantially L-shape with a base portion for receiving a user's foot and a leg portion extending transverse from the base portion for receiving the user's lower leg, said leg portion being sized to extend to a height above the user's ankle;
    b) a support structure including a semi-rigid support member that is integrated with said leg portion of said flexible sock and that is configured to extend upward along the user's leg to a height at or below the height of said leg portion;
    c) said support structure further including a semi-rigid foot pad that is connected to said semi-rigid support member and that is integrated with said base portion of said flexible sock and that is configured to support a bottom of the user's foot such as to provide dorsal assist of the foot in the frontal plane to assist lifting of the user's forefoot from falling downward due to the semi-rigid support member of the lower extremity garment being supported along the user's leg, while the semi-rigid foot pad is supported by the semi-rigid support member such as to provide said dorsal assist;
    d) said semi-rigid foot pad including:
    medial and lateral side flanges at medial and lateral sides of the semi-rigid foot pad; and
    e) said support structure being fixedly connected to said flexible sock such that the support structure, including the semi-rigid foot pad and the semi-rigid support member, and the flexible sock together form an integrated lower extremity garment, having the support structure integrated with said flexible sock, that is configured to be slid over the end of the user's foot with the user's toes placed into an open end of the flexible sock and the integrated lower extremity garment then slid over the user's foot.

2. The lower extremity garment of claim 1, wherein said flexible sock is configured to fully envelop the user's entire foot and lower leg to said height above the user's ankle, wherein said support structure being fixedly connected to said flexible sock involves being removably or non-removably connected thereto.

3. The lower extremity garment of claim 2, wherein said garment is sized to be worn within footwear including shoes or sneakers, wherein said semi-rigid support member is covered by said flexible sock when worn by the user, and wherein said support structure being fixedly connected to said flexible sock by involves being integrally attached thereto by at least one of mechanical connection, adhesive, molding and/or heat-bonding.

4. The lower extremity garment of claim 3, wherein said garment is configured to have a width of less than 3.5 mm along medial and lateral sides thereof.

5. The lower extremity garment of claim 1, further including at least one strap member configured to surround at least a portion of the leg portion when worn.

6. The lower extremity garment of claim 5, wherein said at least one strap member includes at least one adjustable strap member, and wherein said at least one adjustable strap member extends over said flexible sock, such that the strap is adjustable by the user while said lower extremity garment is worn by the user with the user's foot and ankle within the flexible sock.

7. The lower extremity garment of claim 1, wherein said support structure further includes a heel cup proximate a rear of the semi-rigid foot pad that includes raised edges that extend upwardly at least about 10 mm on medial and lateral sides of the user's heel.

8. The lower extremity garment of claim 1, wherein said said semi-rigid foot pad includes an arcuate arch support portion proximate a middle of the semi-rigid foot pad.

9. The lower extremity garment of claim 8, wherein said support structure further includes a heel cup proximate a rear of the semi-rigid foot pad that includes raised edges that extend upwardly at least about 10 mm on medial and lateral sides of the user's heel.

10. The lower extremity garment of claim 9, wherein said semi-rigid foot pad further includes a cushion pad along a top surface of the semi-rigid foot pad.

11. A method for supporting the ankle of a user, comprising:
    a) providing a lower extremity garment, including:
    a flexible sock configured to surround at least a user's foot and ankle, said flexible sock having a substantially L-shape with a base portion for receiving a user's foot and a leg portion extending transverse from the base portion for receiving the user's lower leg, said leg portion being sized to extend to a height above the user's ankle;

a support structure including a semi-rigid support member that is integrated with said leg portion of said flexible sock and that is configured to extend upward along the user's leg to a height at or below the height of said leg portion;

said support structure further including a semi-rigid foot pad that is connected to said semi-rigid support member and that is integrated with said foot base portion of said flexible sock and that is configured to support a bottom of the user's foot such as to provide dorsal assist of the foot in the frontal plane to assist lifting of the user's forefoot from falling downward due to the semi-rigid support member of the lower extremity garment being supported along the user's leg, while the semi-rigid foot pad is supported by the semi-rigid support member such as to provide said dorsal assist;

said semi-rigid foot pad including medial and lateral side flanges at medial and lateral sides of the semi-rigid foot pad; and said support structure being fixedly connected to said flexible sock such that the support structure, including the semi-rigid foot pad and the semi-rigid support member, and the flexible sock together form an integrated lower extremity garment, having the support structure integrated with said flexible sock, that is configured to be slid over the end of the user's foot with the user's toes placed into an open end of the flexible sock and the integrated lower extremity garment then slid over the user's foot; and b) placing the lower extremity garment on the lower leg of the user while said support structure is fixedly connected to said flexible sock such that the support structure and the flexible sock together form the integrated lower extremity garment, by sliding the integrated lower extremity garment over the end of the user's foot with the user's toes placed into the open end of the flexible sock and then sliding the integrated lower extremity garment over the user's foot.

12. The method of claim 11, further including providing dorsal assist of the user's foot in the frontal plane with said lower extremity garment.

13. The method of claim 11, further including providing arch support for the user with said lower extremity garment.

14. The method of claim 11, further including providing cushioning under the sole of the user's foot with said lower extremity garment.

15. The method of claim 11, further including after placing the lower extremity garment on the lower leg of the user having the user extend the user's foot with the lower extremity garment into footwear from the group consisting of a shoe, a sneaker and a boot, including that the thickness of the lower extremity garment around each of the lateral sides of the user's foot is not more than about 4.0 mm.

16. A lower extremity garment, comprising:
a) a flexible sock configured to surround at least a user's foot and ankle, said flexible sock having a substantially L-shape with a base portion for receiving the user's foot and a leg portion extending transverse from the base portion for receiving the user's lower leg;
b) a support structure that includes a semi-rigid support member integrated with the flexible sock in said leg portion, said semi-rigid support member extending upward from the user's heel up to a position above the user's ankle;

c) said support structure further including a semi-rigid foot pad connected to said semi-rigid support member integrated with the flexible sock in said base portion and configured to support a bottom of the user's foot;

d) wherein said lower extremity garment is configured to provide dorsal assist of the user's foot to assist lifting of the forefoot of the user from falling downward including the semi-rigid support member being retained along the user's lower leg while being fixedly connected to said flexible sock which surrounds the user's lower leg such that said semi-rigid foot pad connected to said semi-rigid support member provides said dorsal assist;

e) wherein said semi-rigid foot pad includes medial and lateral flanges formed by raised borders of the semi-rigid foot pad on the medial and lateral sides of the semi-rigid foot pad such as to reduce inversion and eversion at the user's sub-talar joint, said medial and lateral flanges being raised a height sufficient to fix the position of the user's foot on the semi-rigid foot pad; and f) said support structure being fixedly connected to said flexible sock such that the support structure, including the semi-rigid foot pad and the semi-rigid support member, and the flexible sock together form an integrated lower extremity garment, having the support structure integrated with said flexible sock, that is configured to be slid over the end of the user's foot with the user's toes placed into an open end of the flexible sock and the integrated lower extremity garment then slid over the user's foot.

17. The lower extremity garment of claim 16, wherein said flexible sock is configured to surround at least a portion of the user's foot and to extend above a height of the user's ankle, and wherein said support structure being fixedly connected to said flexible sock involves being removably or non-removably connected thereto.

18. The lower extremity garment of claim 17, wherein said garment is sized to be worn within footwear including shoes or sneakers, wherein said semi-rigid support member is covered by said flexible sock portion when worn by the user, and wherein said support structure being fixedly connected to said flexible sock involves being integrally attached thereto by at least one of mechanical connection, adhesive, molding and/or heat-bonding.

19. The lower extremity garment of claim 18, wherein said garment is configured to have a width of less than 3.5 mm along medial and lateral sides thereof.

20. A method for supporting the ankle of a user, comprising:
placing the lower extremity garment of claim 16 on the lower leg of the user, while said support structure is fixedly connected to said flexible sock such that the support structure and the flexible sock together form an integrated lower extremity garment, by sliding the integrated lower extremity garment over the end of the user's foot with the user's toes placed into an open end of the flexible sock and then sliding the integrated lower extremity garment over the user's foot.

21. The method of claim 20, further including providing dorsal assist of the user's foot in the frontal plane with said lower extremity garment.

22. The method of claim 21, further including providing arch support for the user with said lower extremity garment.

23. The method of claim 20, further including providing cushioning under the sole of the user's foot with said lower extremity garment.

24. The method of claim 20, further including at least one of:
  a) said support structure including a heel cup configured to stabilize the user's foot that includes raised edges that extend upwardly at least about 10 mm on both medial and lateral sides of the user's heel; and
  b) said semi-rigid foot pad including an arched central region configured to support the arch of the user's foot.

25. The method of claim 20, further including after placing the lower extremity garment on the lower leg of the user having the user extend the user's foot with the lower extremity garment into footwear from the group consisting of a shoe, a sneaker and a boot, including that the thickness of the lower extremity garment around each of the lateral sides of the user's foot is not more than about 4.0 mm.

* * * * *